US008306853B2

(12) United States Patent
Young et al.

(10) Patent No.: US 8,306,853 B2
(45) Date of Patent: Nov. 6, 2012

(54) METHODS FOR TESTING OPHTHALMIC LENSES

(75) Inventors: John Young, Palm Harbor, FL (US); Daryl Neely, Lithia, DE (US)

(73) Assignee: Colts Laboratories, Clearwater, FL (US)

( * ) Notice: Subject to any disclaimer, the term of this patent is extended or adjusted under 35 U.S.C. 154(b) by 2448 days.

(21) Appl. No.: 11/061,266

(22) Filed: Feb. 17, 2005

(65) Prior Publication Data

US 2005/0179154 A1   Aug. 18, 2005

Related U.S. Application Data

(60) Provisional application No. 60/545,067, filed on Feb. 17, 2004.

(51) Int. Cl.
*G06Q 10/00* (2012.01)
(52) U.S. Cl. ...................................... 705/7.41; 705/7.38
(58) Field of Classification Search ................. 705/7.38, 705/7.41
See application file for complete search history.

(56) References Cited

U.S. PATENT DOCUMENTS

| 3,791,193 | A | * | 2/1974 | Bole | 73/12.13 |
| 3,871,208 | A | * | 3/1975 | Berg | 73/12.13 |
| 3,999,420 | A | * | 12/1976 | Wright | 73/12.14 |
| 4,168,339 | A | * | 9/1979 | Kerko et al. | 428/220 |
| 4,212,919 | A | * | 7/1980 | Hoda | 428/410 |
| 4,320,463 | A | | 3/1982 | Himmelstein | |
| 5,268,335 | A | | 12/1993 | Kerko et al. | |
| 5,555,504 | A | | 9/1996 | Lepper et al. | |

OTHER PUBLICATIONS

Vision Council of America, "Lens Impact Resistance Compliance Guide", printed 2001.*
"The power and value of environmental health and safety audits", Rainer et al., published May/Jun. 2000 in Chemical Health & Safety.*

* cited by examiner

*Primary Examiner* — Beth V Boswell
*Assistant Examiner* — Adrian McPhillip
(74) *Attorney, Agent, or Firm* — Cuenot, Forsythe & Kim, LLC; Stanley A. Kim

(57) ABSTRACT

What has been developed is a method for testing ophthalmic plastic lenses and ophthalmic plastic lens-making processes for compliance with federal safety performance requirements. The method of the invention provides an easier, less costly, and more effective means for complying with these safety performance requirements than what current methods provide.

18 Claims, 2 Drawing Sheets

METHODS FOR TESTING OPHTHALMIC LENSES

CROSS-REFERENCE TO RELATED APPLICATIONS

The present application claims the priority of U.S. provisional patent application No. 60/545,067 filed on Feb. 17, 2004.

FIELD OF THE INVENTION

The invention relates generally to the fields of ophthalmology and product validation. More particularly, the invention relates to a method for testing plastic ophthalmic lenses for compliance with Food and Drug Administration (FDA) safety performance requirements.

BACKGROUND OF THE INVENTION

A few decades ago, in an attempt to reduce the number of eye injuries, the FDA was charged with enforcing new regulations governing plastic lenses used in eyeglasses. Among these regulations, 21 CFR §801.410 sets out an impact resistance requirement and test method which involves dropping a ⅝ inch steel ball onto the finished or uncut finished lens from a height of 50 inches (commonly referred to as the "Drop Ball Test"). With regard to plastic lenses, 21 CFR §801.410 allows statistical batch testing to be completed on a batch basis by the lens manufacturer. This testing is typically performed on a daily/per batch basis.

At the time 21 CFR §801.410 was introduced, lens technology was fairly simple. Accordingly, lens manufacturers and not downstream processors took responsibility for assuring lens compliance with 21 CFR §801.410. Over the ensuing years, lens technology grew increasingly complex. Numerous new plastics, other refractive materials, and hard coats became available. New methods of curing lenses and hard coats, and of applying anti-reflective treatments and other lab-applied treatments came into use. As the number of materials, treatments, and equipment increased in the field, it became increasingly difficult for lens manufacturers to guarantee compliance with 21 CFR §801.410 for all of the combinations of treatments on the same lens. As a result, lens manufacturers more frequently place the burden of impact compliance proof on subsequent processors.

The FDA recommends that lens manufacturers and subsequent processors use the ANSI/ASQ Z1.4 sampling plan which is an acceptance sampling system to be used with switching rules on a continuing stream of lots for Acceptance Quality Limit (AQL) specified. Use of the ANSI/ASQ Z1.4 sampling plan, however, requires such a large sample size that the sampling plan becomes economically unfeasible for the manufacturer. Manufacturers using the ANSI/ASQ Z1.4 sampling plan typically spend $80,000 to 130,000 per year to perform the testing. Therefore, a standard, affordable methodology by which laboratories, manufacturers, and importers can assure that their products comply with the minimum performance requirements set forth in 21 CFR §801.410 is highly desirable.

SUMMARY

The invention relates to a method for evaluating the impact resistance of a batch of plastic ophthalmic lenses. A first step in the method includes selecting from the batch a sample set of lenses to be tested, the number of lenses in the sample set being less than about 5.3% of the number of lenses in the batch. Additional steps in the method include subjecting each lens in the sample set to an impact resistance test and determining the number of lenses from the sample set that pass the impact resistance test, wherein the batch of lenses is deemed to be impact resistant if the number of lenses that fail the impact resistance test is zero if the batch contains less than 3201 lenses, and no more than one if the batch contains 3201 or more lenses. Preferred methods of the invention include providing a lens manufacturer with a plurality of standard operating procedure guidelines to assist the manufacturer in implementing a quality control system. The method of the invention can be used by lens manufacturers to insure that their plastic ophthalmic lenses and lens-making processes comply with FDA minimum performance requirements and involves statistical sampling of the lenses. The method insures product compliance with FDA regulations while reducing a manufacturer's testing costs through statistically valid sampling plans based on published FDA guidelines that greatly reduce the number of lenses requiring testing.

The method of the invention also includes several process control steps for verifying a lens manufacturer's continued compliance with the FDA guidelines. These process control steps include yearly audits of the lens manufacturer's facility and lens-making processes by an auditing entity (e.g., an independent test laboratory), and regular testing (e.g., every three months) performed by the auditing entity of the manufacturer's lenses. The method of the invention further includes a compliance certification issued by the auditing entity to a manufacturer that has successfully met the auditing entity's performance requirements.

Accordingly, the invention features a method for evaluating the impact resistance of a batch of plastic ophthalmic lenses. The method includes the steps of: (a) selecting from the batch a sample set of lenses to be tested, wherein the number of lenses in the sample set is less than about 5.3% of the number of lenses in the batch; (b) subjecting each lens in the sample set to an impact resistance test; and (c) determining the number of lenses from the sample set that pass the impact resistance test, wherein the batch of lenses is deemed to be impact resistant if the number of lenses that fail the impact resistance test is zero if the batch contains less than 3201 lenses, and no more than one if the batch contains 3201 or more lenses.

When the number of lenses contained in the batch is in the range of about 151 to about 280, the size of the sample set can be in the range of about 6 to about 9 lenses (e.g., 8 lenses). When the number of lenses contained in the batch is in the range of about 281 to about 500, the size of the sample set can be in the range of about 9 to about 11 lenses (e.g., 10 lenses). When the number of lenses contained in the batch is in the range of about 501 to about 1200, the size of the sample set can be in the range of about 11 to about 14 lenses (e.g., 12 lenses). When the number of lenses contained in the batch is in the range of about 1201 to about 3200, the size of the sample set can be in the range of about 14 to about 26 lenses (e.g., 15 lenses). When the number of lenses contained in the batch is in the range of about 3201 or more, the size of the sample set can be in the range of about 26 to about 30 lenses (e.g., 28 lenses).

The batch can have an AQL in the range of about 0.5% to about 1.5%. When the number of lenses contained in the batch is in the range of about 151 to about 280, the batch can have an AQL of about 0.6%. When the number of lenses contained in the batch is in the range of about 281 to about 500, the batch can have an AQL of about 0.6%. When the number of lenses contained in the batch is in the range of about 501 to about 1200, the batch can have an AQL of about 0.4%. When the number of lenses contained in the batch is in the range of about 1201 to about 3200, the batch can have an AQL of about 0.3%. When the number of lenses contained in the batch is in the range of about 3201 to about 1 million, the batch can have an AQL of about 1.3%.

In the method of the invention, the steps of selecting from the batch a sample set of lenses to be tested, subjecting each lens in the sample set to an impact resistance test, and determining the number of lenses from the sample set that pass the impact resistance test can be performed by the lens manufacturer. The method can further include the steps of: (d) providing to the lens manufacturer a plurality of formal operating procedure guidelines governing process control in a process of manufacturing and testing of the lenses; and (e) periodically having a party independent of the lens manufacturer verify that the lens manufacturer is adhering to the formal operating procedure guidelines.

In another aspect, the invention features a method for evaluating the impact resistance of a batch of plastic ophthalmic lenses. This method includes the steps of: (a) providing from a lens manufacturer to an independent testing laboratory a first plurality of lenses, the first plurality containing a number of lenses in the range of about 50 to about 60; (b) having the independent testing laboratory determine the mean fracture height of the first plurality of lenses using an impact resistance test; (c) providing from the lens manufacturer to the independent testing laboratory a second plurality of lenses, the second plurality containing a number of lenses in the range of about 10 to about 15, wherein the first and second pluralities of lenses are produced according to the same method; and (d) having the independent testing laboratory determine the mean fracture height of the second plurality of lenses.

Unless otherwise defined, all technical terms used herein have the same meaning as commonly understood by one of ordinary skill in the art to which this invention belongs.

By the term "manufacturer" is meant an entity that treats the lenses for fitting into lens frames. A "manufacturer" is also an entity who alters the physical or chemical characteristics of the lens by such acts as grinding, heat treating, beveling, and cutting. Such an entity is commonly known as a surfacing laboratory. A "manufacturer" is also an entity that imports eyeglasses for resale.

By the phrase "lens fracture" is meant a lens that breaks into two or more pieces when struck by a steel ball during impact testing or a lens having material visible to the naked eye that becomes detached from the ocular surface.

Although methods similar or equivalent to those described herein can be used in the practice or testing of the present invention, suitable methods are described below. The particular embodiments discussed below are illustrative only and not intended to be limiting.

DETAILED DESCRIPTION

Figure 1:
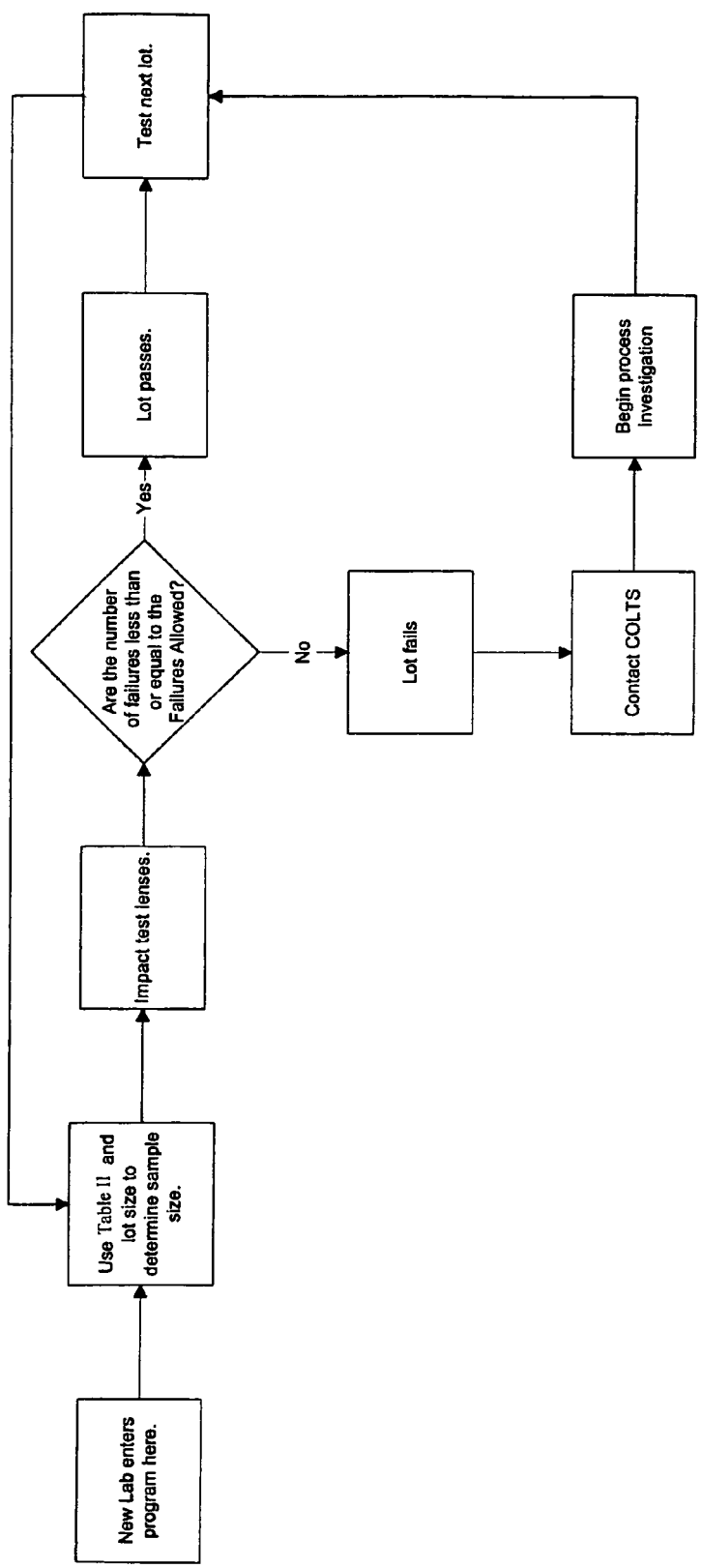
FIG. 1 is a flow chart of sampling and decision making logistics made by a manufacturer using the method of the invention.
Figure 2:
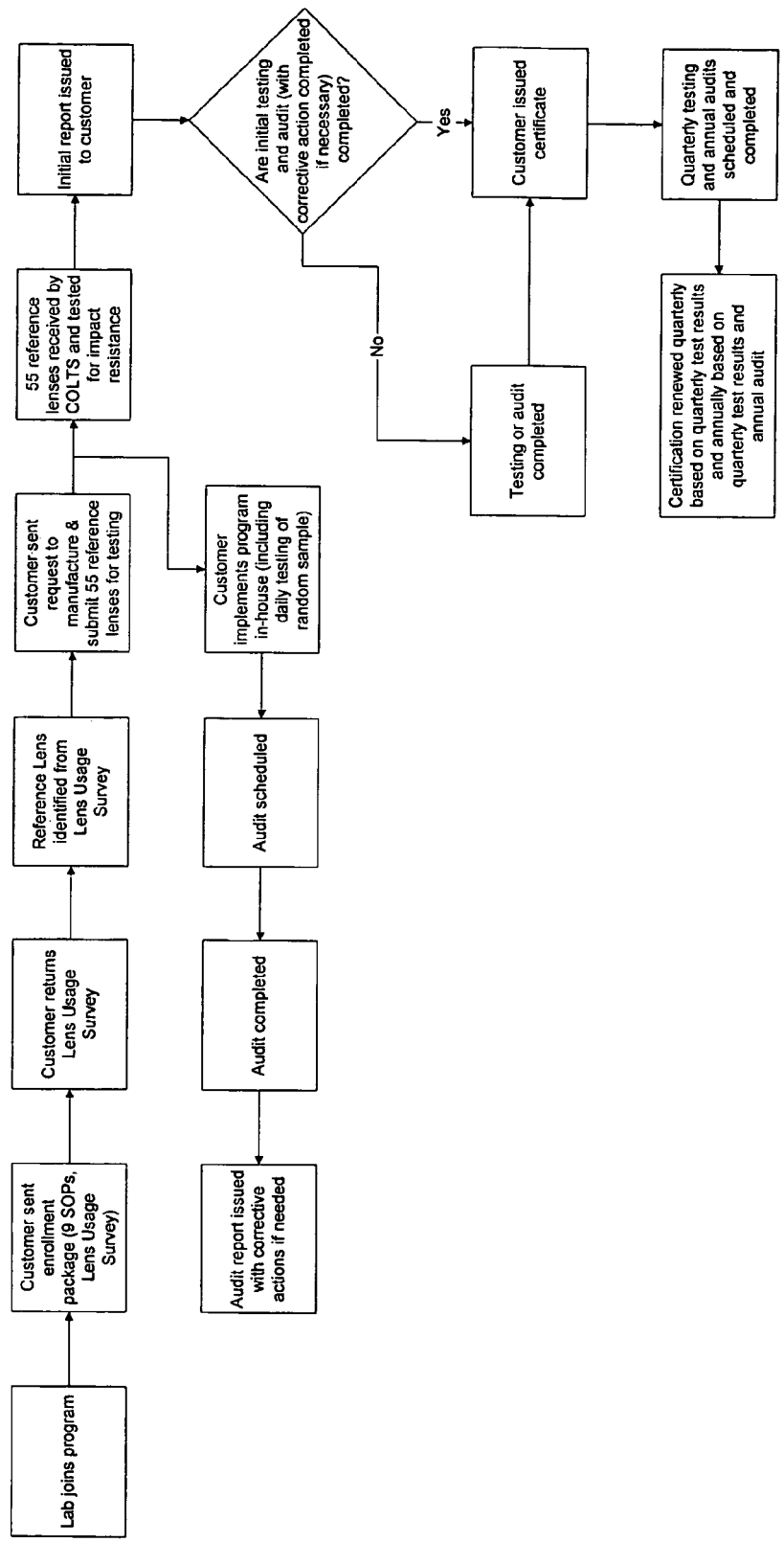
FIG. 2 is a flow chart showing steps of the method of the invention.

The invention encompasses a method for evaluating ophthalmic plastic lenses and ophthalmic plastic lens-making processes for compliance with minimum performance requirements set forth in 21 CFR §801.410. The method of the invention includes a sampling plan that greatly reduces the sampling size compared to currently used methods as well as audits of the lens-making facility (i.e., manufacturer's facility) to insure compliance. Because the sampling size is greatly reduced, the method of the invention provides the ophthalmic industry with a low-cost means for fully complying with 21 C.F.R. 801.410. Lens manufacturers typically spend $80 to $130,000 per year on lens testing using currently available methods. The method of the invention reduces the manufacturer's cost to approximately $4700 per year. The below described preferred embodiments illustrate adaptations of these methods. Nonetheless, from the description of these embodiments, other aspects of the invention can be developed and/or practiced based on the description provided below.

Method for Testing Ophthalmic Lenses

In a preferred method of the invention, a lens manufacturer wishing to manufacture and/or surface lenses that are in compliance with FDA safety performance requirements (e.g., 21 CFR 801.410) or wishing to evaluate lenses for compliance first provides an auditing entity with information about the lenses that are to be tested. This information typically includes the type of lens and how the lens has been treated (e.g., coatings such as hard coats and anti-reflective coatings). The auditing entity provides the lens manufacturer with a plurality of standard operating procedures useful for implementing a Quality System (i.e., procedures, materials and equipment for producing lenses) that meets the requirements of the FDA compliance certification program. The standard operating procedure guidelines (presented as Examples 1-11) describe all aspects of sampling, impact testing, auditing, corrective action, preventive maintenance, data records and retention, process control and program requirements to achieve and maintain certification. The lens manufacturer can adopt this documented Quality System in its entirety or augment its own preexisting quality control system with the standard operating procedure guidelines provided by the auditing entity. The appropriate lens manufacturer personnel (e.g., management) reviews the Quality System procedures and begins implementation.

The lens information provided to the auditing entity is used by the auditing entity to identify the "reference lens" that the manufacturer will provide for testing. By providing the auditing entity with this information, the auditing entity is able to make a reasonable estimate of the manufacturer's weakest lens configuration (i.e., the reference lens). In preferred methods of the invention, the auditing entity maintains a database of various lens treatments and their effects on impact resistance. Once identified, the lens manufacturer makes approximately 55 (e.g., 50, 51, 52, 53, 54, 55, 56, 57, 58, 59, 60, etc.) reference lenses. These reference lenses are a homogenous sample (i.e., have the same surface and are subjected to the same treatment or treatments). These lenses are then sent to the auditing entity for testing and statistical analysis. Typically, the auditing entity tests these 55 lenses using an appropriate impact test, e.g., Variable Height Impact Testing. This impact testing protocol is described in further detail in Example 3.

In preferred methods, the results of the Variable Height Impact Testing are then analyzed using probit statistics to determine the mean fracture height (i.e., the $50^{th}$ percentile). This mean fracture height sets the baseline for process performance for the lens manufacturer. The auditing entity then contacts the lens manufacturer that has submitted the 55 reference lenses and schedules an on-site audit of the Quality System implemented by the lens manufacturer. A preferred auditing protocol is described in Example 6. This independent, third party on-site audit verifies that the Quality System used by the lens manufacturer complies with the guidelines set forth in the standard operating procedures. The audit program assures that record retention, test methods, equipment maintenance, preventive actions, corrective actions, and product disposition are being properly followed. A report of the auditing results is generated by the auditing entity and given to the lens manufacturer. Once the audit is successfully completed and the reference lens performance has been determined, the lab is awarded Certified Status.

According to the method of the invention, a lens manufacturer conducts daily random sampling of their lenses to maintain Certified Status. Random sampling is conducted on a daily basis by the lab with sample sizes determined using the sampling plan described in the section below (Sampling Plan for Testing Ophthalmic Lenses) as well as in Example 4. Any failures noted during daily random sampling are reported as soon as possible (e.g., immediately) to the auditing entity. In a typical method of the invention, the cause for the failure is investigated and actions to correct the failure (i.e., corrective actions) are taken.

Another aspect of maintaining Certified Status is reference lens testing that is conducted by the auditing entity several times a year, preferably every three months (i.e., quarterly testing). In a typical method of the invention, the auditing entity notifies the lens manufacturer to submit 12 reference lenses for testing approximately 30 days (e.g., 15, 17, 19, 21, 23, 25, 27, 29, 30, 31, 33, 35, etc.) prior to the scheduled date for testing (e.g., quarterly testing). The auditing entity then subjects the lenses to impact-testing and subjects the impact-testing results to an appropriate statistical analysis (e.g., statistical probit analysis). Audits are conducted by auditing entity personnel to verify compliance with the Quality System requirements of the auditing entity. On-site audits are preferably conducted in accordance with the protocol in Example 6, however, any suitable auditing protocol can be used. Once the audit and the quarterly process control testing are successfully completed, the lens manufacturer is re-certified. Certification is therefore granted every several months (e.g., every three months).

Sampling Plan for Testing Ophthalmic Lenses

Industry compliance with 21 CFR 801.410 has been a challenge due to the cost that testing lenses represents to lens manufacturers using Normal Inspection Level II Single Sample (ANSI/ASQ Z1.4). Because a small sample size is necessary and desirable in order to drive down the cost of compliance at the manufacturer, the method of the invention addresses the cost issue by employing a sampling plan that allows for smaller sample sizes which will not place undo financial hardships upon manufacturers. In traditional sampling plans, smaller sample sizes lead to larger sampling risks where consumer protection is concerned. The sampling plan of the invention, however, addresses the need to have a reduced sample size while maintaining consumer protection at equal or better levels than those provided by traditional sampling plans. By reducing the sample size the manufacturers are required to use, the producer risk associated with a smaller sample size (and smaller accept number) is increased. At the same time, consumer protection is maintained at equal or better levels than the sampling plan currently accepted by the FDA.

Sampling plans are used to make product disposition decisions. They determine which lots of product to accept and release and which lots to reject and discard. Ideally, a sampling plan should reject all "bad" lots while accepting all "good" lots. However, because the sampling plan bases its decision on a sample of the lot and not the entire lot, there is always a chance of making an incorrect decision. The behavior of a sampling plan is described by the sampling plan's Operating Characteristic (OC) curve. On an OC curve, the X axis gives different process percent defectives. The Y axis gives the corresponding probability of acceptance. OC curves are generally summarized by two numbers: the Acceptable Quality Level (AQL) and Lot Tolerance Percent Defective (LTPD), the two points on the OC curve. The AQL represents a level of defects routinely accepted by the sampling plan. Conversely, the LTPD represents a level of defects that is unsatisfactory and therefore should be routinely rejected by the sampling plan. The software accompanying Taylor (Taylor, Wayne A. *Guide to Acceptance Sampling*. Libertyville, Ill., 1992) can be used to obtain the AQL and LTPD of any sampling plan. Any of a number of software packages can be used to evaluate the sampling plan of the invention. An appropriate software package can calculate and display OC curves, AQL and LTPD curves.

The method of the invention includes a sampling plan that places the risk of the product on the manufacturer in order to minimize the sample size for the manufacturer. The FDA has stated that manufacturers of lenses must produce lots (i.e., batches) that have an AQL of or below 6.5%. Using the sampling plan of the invention, the AQL for the manufacturer is in the range of about 0.3% to about 1.3%, and preferably about 0.6%.

In other words, lenses are really only 0.6% defective rather than the 6.5% defective that the FDA allows. Using the sampling plan of the invention, a product that is 6.5% defective will not pass a sampling plan designed for an AQL of 0.6%. The consumer therefore remains protected at levels equal to or better than those using ANSI/ASQ Z1.4 6.5% AQL sampling. In the sampling plan of the invention, lot sizes for the sampling are based on the lot sizes (letter codes) found in ANSI/ASQ Z1.4. The accept number for each letter code is then reduced to zero or one (e.g., for larger samples such as those greater than 3201). The sample size and the Acceptance Number are used to develop an OC curve that yields the desired AQLs and LTPDs. This results in a large reduction in the AQL as well as a reduction in the LTPD. The sample size required for each letter code is then adjusted to obtain better LTPDs than those given by the 6.5% AQL sampling plan. The result obtained is a sampling plan with improved AQLs (approximately 0.65% vs. 6.5% of currently used methods) while maintaining superior LTPDs.

A preferred sampling plan of the invention is compared to ANSI Z1.4 in Table I below which shows the results from five OC curves which plot the probability of acceptance versus % defective using ANSI Z1.4 sampling vs. the sampling plan of the invention.

| Lot size | ANSI Z1.4 General Inspection Level II 6.5% | | | | Sampling Plan of the Invention | | | |
|---|---|---|---|---|---|---|---|---|
| | Sample size | Acceptance number | AQL | LTPD | Sample size | Acceptance Number | AQL | LTPD |
| 151-280 | 32 | 5 | 8.5 | 27.1 | 8 | 0 | 0.6 | 25.0 |
| 281-500 | 50 | 7 | 8.2 | 22.4 | 10 | 0 | 0.6 | 20.6 |
| 501-1200 | 80 | 10 | 7.9 | 18.6 | 12 | 0 | 0.4 | 17.4 |
| 1201-3200 | 125 | 14 | 7.5 | 16.1 | 15 | 0 | 0.3 | 14.2 |
| 3201 or more | 200 | 21 | 7.6 | 14.1 | 28 | 1 | 1.3 | 13.2 |

*AQLs and LTPDs were calculated using Taylor Enterprises Sampling Program Version 1.0 1992 - Single Sampling Plan for a series of lots Because of the small sample sizes required in methods of the invention, lens samples can be obtained from rejected lenses that the manufacturer would otherwise discard. Current lens-making practices in the ophthalmic industry result in the rejection of approximately 5% of lenses processed at the manufacturer for cosmetic defects (e.g., scratches, coating pits, blemishes, drips). Typically, these rejects have no effect on the impact resistance of the lens. Therefore, samples selected for random testing (e.g., daily testing) can be drawn from these rejected lenses. In fact, at manufacturers that currently practice acceptance sampling, this is the practice today. As there is no reason to believe that such defects are not random in nature, the population to select the random sample from has already been randomized. Randomization would then be further assured by randomly selecting the sample from the random sub-group of the population to be tested.

In preferred methods of the invention, any failures of the randomly sampled lenses are investigated by the manufacturer to determine if there is an assignable cause for the failure. If there is an assignable cause, corrective action is implemented to eliminate (or minimize the likelihood of occurrence of) the cause. If no assignable cause can be identified, approximately 12 (e.g., 12, 13, 14, 15, 20, 30, etc.) lenses of the lens configuration resulting in an impact failure are manufactured and submitted to the auditing entity for testing. The auditing entity determines the critical fracture height using the up-down method (described in Example 10) or other suitable testing method and probit statistics. These results are then used to advise the manufacturer on the proper course to take when processing the product in question.

Regularly scheduled audits are conducted by trained auditors from the auditing entity. Audits include verifying correct application of the sampling plan (e.g., sample size, reaction to failures, data records and retention, etc.). Regular audits insure compliance with 21 CFR 801.410 and aid in the continuous improvement of manufacturer's processes using the method of the invention. Any non-conformances are addressed using an appropriate corrective action program (e.g., the corrective action protocol of Example 7).

Process Control for Testing Ophthalmic Lenses

In addition to daily random testing, the method of the invention includes process control functions to determine if the manufacturer maintains certification. Process control functions include on-site auditing of the manufacturer's facility and lens-making processes through scheduled reference lens testing by the auditing entity (e.g., independent testing laboratory). The on-site audits assure that record retention, test methods, preventive maintenance, corrective actions, and product disposition are being properly followed. Reference lens testing is conducted several times a year and in preferred methods of the invention, on a quarterly basis (i.e., every three months) by the auditing entity (e.g., independent testing laboratory). Typically, 12 reference lenses are manufactured quarterly and submitted to the auditing entity to estimate the critical break height of the group and compared to the baseline testing results from the initial 55 reference lenses. Testing is accomplished using the data from the initial test results to determine the starting point to impact the group of lenses and the standard deviation of the heights of the fractured lenses from the initial test group to determine the amount to increment the height on each lens in the test group. The data is analyzed using probit statistics and the mean fracture height of the group calculated. Audit reports are provided to each manufacturer and each quarterly result is control charted by the auditing entity using Individual-Moving Range control charts to establish the process has remained in a state of control. The manufacturer having no major non-conformances and whose reference lens performance is acceptable is considered critical for achieving and maintaining compliance certification.

Data Collection and Statistical Treatment

In one embodiment of the invention, lenses are impact-tested per the up-down testing method described in Example 10. The purpose of this test methodology is to confirm the level of the critical fracture height. This is accomplished by raising or lowering the drop height based on product result. If the lens fractures, the drop height on the next lens is reduced. If the lens does not fracture, the drop height for the next lens is increased. As a result of building this pattern of breaks and no breaks, a normal distribution emerges about the average fracture height (height required to fracture 50% of the lenses).

The results of breaks and no-breaks are examined for normality using Normality Testing in Minitab Statistical Software. This verifies that proper methodology was used to run the test and that normal process variation is present in the product. The resulting P-value is examined to assure it is greater than 0.05 which represents a pattern of normal data distribution. The preferred statistical treatment for this type of data is probit statistics. Therefore, once normality is proven, the data is analyzed using probit statistics with appropriate software such as Minitab Statistical Software. This analysis is done by coding the data results of fractures (1) and non-fractures (0). Minitab is then used to analyze the coded fracture data using probit statistics. Typically, when the no-break data is coded out of the pattern, the failure mechanism of lenses follows a lognormal data distribution pattern. Therefore, this distribution pattern is used in data analysis of the fracture results. This probit analysis of data results in accurate estimates of the critical fracture height.

EXAMPLES

Example 1

Compliance Program Quality Manual

The policies identified in this Example are applicable to facilities (i.e., manufacturers) using the system of the invention to attain certification by the auditing entity. The policies stated in this document must be followed for the proper operation of the Quality System and to maintain Certified auditing entity Compliance Status.
Materials and Equipment:
    Drop ball test unit compliant to 21 CFR 801.410 and FDA impact test result form.
Authority and Responsibility:
    It is the responsibility of the manufacturer management to communicate the requirements of this program to testing and purchasing personnel. It is the responsibility of the manufacturer management to notify the auditing entity in the event of any lens failure for impact testing. It is the responsibility of the manufacturer management to assure Reference Lens samples are sent to the auditing entity for testing on a scheduled basis. It is the responsibility of the manufacturer management to notify the auditing entity prior to using new processes in a Compliance Certified facility. If the new process is deemed a significant change that could affect the impact strength of product, the Compliance Certified facility must submit 55 reference lenses processed through this new condition to the auditing entity for testing and analysis. It is the responsibility of the manufacturer management to adhere to the center thickness specifications for the reference lens as specified in this program. It is the responsibility of the auditing entity to notify the manufacturer in the event testing shows a condition which indicates a process not in a state of statistical control. It is the responsibility of the auditing entity to issue FDA Compliance Certified status to facilities who participate in the auditing entity program, show acceptable process performance of their Reference Lens, and successfully complete a yearly on-site audit by personnel of the auditing entity. It is the responsibility of the auditing entity to issue quarterly written reports to each manufacturer participating in the auditing entity Compliance Program. It is the responsibility of the auditing entity to notify facilities in the program when quarterly testing is due.
Procedure:
    Initial manufacturer certification and quarterly re-certification is accomplished through a program of product testing, process control testing and on-site audits. Daily testing will be performed by the manufacturer. Results of daily random impact testing performed at the facility will be recorded in an appropriate form. Test records are maintained appropriately. The test equipment at the manufacturer's facility will be maintained appropriately. Processes used in the manufacture of lenses will be monitored appropriately. Records of training should be kept with the procedures for easy access. In addition to product testing at the manufacturer's facility on a daily basis, and quarterly process testing by the auditing entity, the manufacturer's facility will also be audited yearly by personnel of the auditing entity.
Assessment:
    On a quarterly basis, the auditing entity will analyze the process control capabilities of the certified manufacturer based on impact testing results. Any daily test results at the manufacturer showing drop ball failures will be investigated.

Example 2

Compliance Program Certification Requirements

This procedure defines the requirements for achieving and maintaining Certified Manufacturer status through the auditing entity Compliance Certification Program.
Material and Equipment:
    21 CFR 801.410 compliant impact tester and Impact Test Results Form
Pre-Certification:
    Manufacturers seeking FDA Compliance Certification should begin by completing the Enrollment Form and submitting the yearly program payment to the auditing entity. Once these are received, the auditing entity will send the manufacturer a Usage Survey to complete and return as well as all required procedures needed to implement a Quality System that meets the requirements of the Compliance Certification Program. The manufacturer should complete and return the Usage Survey as soon as possible, but not later than thirty days after receipt. Manufacturer management should review the Quality System procedures and begin implementation in as timely a manner as possible. These procedures contain the Program requirements that the manufacturer will be audited to. Any questions regarding the content or implementation of the program should be addressed to the FDA Compliance Program Coordinator or the Program Technical Advisor. Results from the Usage Survey will be used to identify the Reference Lens that manufacturer the will need to use. Once identified, the manufacturer must make 55 reference lenses. These lenses are to be sent to the auditing entity for testing and statistical analysis. The auditing entity will test these 55 lenses using Variable Height Impact Testing.
Certification:
    Results of testing will be analyzed using probit statistics to determine the mean fracture height. This fracture height will set the baseline for process performance for the manufacturer. All data generated from quarterly testing will then be used to create an Individual-Moving Range control chart to evaluate process control at the manufacturer. The auditing entity will contact each manufacturer that has submitted the 55 reference lenses and schedule an on-site audit of the Compliance Program at each manufacturer. On-site audits are conducted. Once the audit is successfully completed and the Refrence Lens performance has been determined, the manufacturer will be awarded Certified Status.
Certification Maintenance:
    Daily Random Sampling: Random sampling will be conducted on a daily basis with sample sizes determined appropriately. Any failures noted during daily random sampling must be reported immediately to the auditing entity. The cause for the failure must be investigated.
    Quarterly Reference Lens Testing: Certification is maintained through quarterly testing of the Reference Lens and performing statistical analysis. Approximately thirty days prior to the scheduled date for quarterly testing, the auditing entity will notify the manufacturer's facility to submit 12 reference lenses for testing. The manufacturer's facility will produce and send the reference lenses to the auditing entity. The auditing entity will test these 12 lenses using Variable Height Impact Testing.
    On-Site Audit: Manufacturers that have submitted all lenses required for quarterly testing will be scheduled for an on-site audit. Audits will be conducted by personnel of the auditing entity to verify compliance to the Quality System requirements. Once the audit and all quarterly process control testing are successfully completed, the manufacturer will be re-certified.

Probation: Manufacturers that have quarterly test lenses repeatedly exhibit out of control characteristics are subject to having their certification placed on probation. Probation can be lifted when the manufacturer submits quarterly samples that exhibit in control characteristics. Corrective action may also be requested to document actions taken to return the process to control. Manufacturers that have major non-conformances issued during the FDA Compliance audit are subject to having their certification placed on probation. Probation can be lifted when corrective action is submitted to the auditing entity identifying the root cause of the non-conformance along with the corrective actions taken (or to be taken) to insure no re-occurrence of the root cause. An additional audit may be necessary to verify the effectiveness of the corrective action. Manufacturers that fail to submit quarterly reference lenses in a timely manner are subject to having their certification placed on probation. Manufacturers placed on probation are not covered by the Compliance Program warranty for the period of the probation.

Suspension of Certification: Manufacturers that are on probation are subject to having their certification suspended. Certification can be suspended for the following reasons: efforts to have quarterly submission of reference lenses have been unsuccessful, corrective action to a non-conformance is found to be lacking in addressing the root cause of the non-conformance, and corrective action to a non-conformance is not submitted in a timely manner. Manufacturers placed on suspension are not covered by the Compliance Program warranty for the period of the suspension.

Revocation of Certification: Manufacturers that are on suspension are subject to having their certification revoked. Certification can be revoked for the following reasons: repeated efforts to have quarterly submission of reference lenses have been exhausted, corrective action to a non-conformance is found to be lacking in addressing the root cause of the non-conformance and repeated effort to correct the situation have been unsuccessful, corrective action to a non-conformance is not submitted in a timely manner and repeated efforts to have corrective action submitted have been unsuccessful. Manufacturers that have had certification revoked are no longer covered by the FDA Compliance Program warranty. Manufacturers that have had their certification revoked and desire to obtain certification again, must begin the program as a new manufacturer seeking certification would.

Termination from the Program: Manufacturers may be terminated from the program for any of the following reasons: failure to submit 55 reference lenses for testing in a timely manner, failure to schedule the initial FDA Compliance audit in a timely manner, and failure to adequately respond to major non-conformances on the initial FDA Compliance audit after repeated attempts.

The manufacturer must notify the auditing entity when new equipment that is used in lens processing is obtained to assure this new equipment does not adversely affect process control limits created using the old equipment. Upon determination that this new equipment could potentially affect the process control limits, the manufacturer will produce 55 reference lenses using the new equipment and send these lenses to the auditing entity for evaluation. Upon impact testing and analysis, the auditing entity will determine if the new equipment produces product with performance characteristics equivalent to the previous equipment. If performance of the new equipment is determined to be different than the old equipment, a new baseline for the process will be established.

The manufacturer must notify the auditing entity when it moves to a different location. It must submit 55 reference lenses to the auditing entity for evaluation against pre-established process control limits. If the old limits still apply, the results are documented and quarterly testing resumes as normal. If the results from the new manufacturer yield different Process Limits, these new limits become the new Process Limits. The manufacturer must notify the auditing entity in the event of a major process change, which could have an effect on the impact strength of the product. The following are examples of, but not an all inclusive list of, major process changes: time or pressure changes to generating, fining or polishing outside of normal process parameters, permanent changes to the polishing compound or polishing pads, and changes in the coating or curing time or temperatures outside of normal process parameters.

Example 3

Impact Testing

A test to determine the ability of a lens to meet FDA impact resistance requirements and the method used to record the results.

Materials and Equipment:

50 inch FDA impact tester, 5/8 inch stainless steel ball, FDA Impact Test Result Form, FDA Impact Test Failure Form, and digital center thickness gauge with two (2) decimal place resolution using a millimeter scale.

Procedure:

Select a random sample from reject lenses to impact test. The number of lenses required is determined using the sampling procedure described below in Example 4. Lenses selected must be random in nature, and representative of the manufacturer's production. This is assured by randomly selecting lenses that have been rejected. Lenses that have been rejected for anything that would alter impact strength (e.g., center thickness too thin or thick, lenses with stress fractures, etc.) must not be used as part of the sample. Assure the lenses are at room temperature before impact testing them. Assign a number to each lens by marking them with a permanent marker on the edge of the convex side. Provide the following information on an appropriate form prior to testing: lot size, sample size, test date, shift, name or initials of technician performing the test, lens manufacturer, lens material, lens type (SV, Bifocal, Trifocal, Progressive, Other), lens power (Sphere/Cylinder/Add), coating applied (enter "None" or "N/A" if no backside coating is used), anti-reflective coating (enter "None" or "N/A" if no AR coating is used), and individual lens center thickness.

Prior to testing, insure that the concave surface of the lens does not come into contact with anything other than the gasket on the support tube. Visually center the test lens over the lens support base—convex side up. Impact the lens from fifty inches. Note: Fractures should be recorded with an "F" on the Impact Test Result Form, non-fractures should be recorded with an "P". All ball drops will be from fifty inches. All lenses will be impacted once only. Impact all lenses and record the results. Circle the appropriate disposition for the lot (passes or fails) on the data sheet. In the event of a failure in the random sample, proceed as follows: complete all information on an appropriate form, contact the auditing entity to inform them of the failure, begin an investigation of the process to determine the cause of the failure, contact the auditing entity with the results of the process investigation (or within ten working days to update the auditing entity on the status of the investigation), and document the cause of the failure (if it can be determined) and corrective action using an appropriate form. If no cause can be determined, contact the auditing entity for further instructions.

Assessment and Calculation:

A lens fracture is any lens that fractures from the convex to the concave surface and separates into two or more pieces. A lens fracture is also any lens having material that becomes detached from the concave side. Record all test results and store records. Investigate lens fractures per guidelines above. Make a lot Pass/Fail determination.

Example 4

Impact Test Sampling

To implement a statistically valid method of sampling in order to be in compliance with FDA Impact Resistance Regulation 21 CFR 801.410. This plan is intended to be complemented by quarterly reference lens testing to insure a stable process and regular audits to insure compliance to 21 CFR 801.410.

Procedure:

The batch size can be defined as the number of lenses produced per shift, per day or per week. NOTE: the auditing entity recommends defining a batch as one day's production. This simplifies the tracking of product in case of an impact failure. Sample size determination will be based on Table II below.

| IMPACT TESTING Lot size | SAMPLING PLAN Sample size | Failures allowed |
|---|---|---|
| 151-280 | 8 | 0 |
| 281-500 | 10 | 0 |
| 501-1200 | 12 | 0 |
| 1201-3200 | 15 | 0 |
| 3201 or more | 28 | 1 |

Following the flowchart of FIG. 1, begin testing lenses. New manufacturers (e.g., labs) in the program start at the "New Lab (i.e., manufacturer) enters program here" box. Lenses used for testing are randomly selected. Reject lenses may be used if the lens has not been rejected for a reason that would affect impact strength. Normally lenses rejected for minor cosmetic defects (pits, scratches, coating drips, etc.) are acceptable for testing. Table III below can be used as guidance for selecting appropriate sample lenses.

| Reject class | Item | Description | Acceptable for testing using the system of the invention |
|---|---|---|---|
| Process cosmetic Non-random | Grey | Lack of complete polishing or fining | No |
| | Blocking ring | Pressure or curve related defect | No |
| | Gen. Pit | Chatter during generating the surface | No |
| | Delamination | Non-adherence of coating | No |
| | Crazing | Cracking of coating | No |
| | Distortion | Production caused optical flaw | No |

| Reject class | Item | Description | Acceptable for testing using the system of the invention |
|---|---|---|---|
| Accidental cosmetic Random | Scratch | Caused from poor handling | Yes |
| | Bubble | Coating defect from original lens manuf. | Yes |
| | Chip | Chip to edge from poor handling | Yes |
| | US | Unidentified substance* | Yes |
| | Cotton | Somewhat larger than US | Yes |
| | Striation | Internal plastic flaw | Yes |
| | Weld line | Internal polycarbonate flaw | Yes |
| | Fern | Molding defect from original lens manuf. | Yes |
| | Demold | Molding defect from original lens manuf. | Yes |
| | Mold stain | Molding defect from original lens manuf. | Yes |

*US is air born dust and particulate that may become lodged in the coating.

Reject lenses used for testing must be in their finished form (i.e., surfaced, edged and coated according to the original prescription). NOTE: Lenses selected for testing must be representative of the make-up of the batch they represent. They must not be all the same material and coating. Reject lenses must meet center thickness specifications. If a lens does not meet center thickness specifications, do not impact test it. Select another lens from the reject lenses. Lenses are drop ball tested per 21 CFR 801.410. Use the procedure in Example 3 for impact testing lenses. Keep track of the information related to every lens tested. Store all completed Impact Test Report Forms properly. Assessment and Calculation: Batches will be dispositioned according to the sampling plan found in Table II.

Example 5

Impact Test Equipment Maintenance

This procedure covers the checks and calibration steps that must be accomplished to assure the proper operation of the drop ball test equipment. Proper operation and condition of the test unit is vital in producing reliable results.

Materials and Equipment:

FDA Compliant Drop Ball Test Unit, neoprene gasket, and ⅝" diameter steel ball.

Procedure:

Daily Maintenance is performed on the test unit prior to testing product. Results of this section are recorded on the Daily Maintenance Check Sheet. Visually inspect the neoprene gasket to assure it is free of tears or cracks and is securely bonded to the support tube.

Change the gasket if it is damaged in any way. If the gasket is changed note the date of the change in the comments section of the Daily Maintenance Check Sheet. Bond the gasket if any part is loose. Check the condition of the ⅝" steel ball. Roll the steel ball on a flat surface to assure there are no flat spots. If flat spots are observed, change the steel ball. Visually inspect the steel ball for signs of rust or other damage. Replace if necessary. Assure the lens, when positioned with the concave surface of the lens on the support tube, does not come in contact with anything other than the gasket on the support tube. In order to verify the steel ball is dropping within a 5/8" diameter circle of geometric center dot a "dummy" lens on geometric center. Place the "dummy" lens visually centered (using the dot) on the support tube with its convex surface facing up. Drop the steel ball from 50" and using a ruler make sure it is striking the lens within a 5/8" diameter circle located at the geometric center of the lens. If the ball is not striking within this diameter, adjust the position of the test unit so it does. Yearly Calibrations are performed to assure the dimensions critical to the test have not changed from the last time they were measured. Results of this section are recorded on a Yearly Calibration Check Sheet. Using calipers or micrometers, measure the diameter of the steel ball. Assure the steel ball has a nominal diameter of 5/8 inch. Assure that the base plate and its rigidly attached fixtures weigh at least twenty-seven pounds. Measure that the drop distance between the drop point and the upper surface of the test lens positioned on the support tube is a minimum of fifty inches. If the test unit uses a guide tube to guide the fall of the steel ball, insure the tube does not restrict the fall of the ball. The test tube shall be at least four inches from the lens surface when the lens is positioned on the support tube for testing. Change out the gasket on the support tube yearly (or sooner if the gasket is worn or torn) and record the date.

Example 6

Certification Audit

This Example defines the guidelines for performing and documenting an on site audit at manufacturers using the system of the invention. This audit is performed on a scheduled basis at the participating manufacturer. Results are communicated to the manufacturer's management through a final verbal review before the auditor leaves the location and through a formal audit report sent to the customer from the auditing entity.
Procedure:
Quality Audit: Aspects of the Quality System shall be reviewed on a regular basis by means of planned and documented assessments. A written report of findings shall be developed and forwarded to Senior Manufacturer Management. Non-conformances found during audits should be immediately brought to the attention of the individual incharge of the area being assessed. If the item can not be immediately resolved to the satisfaction of the assessor, it must be documented and followed up until proper resolution takes place.
Audit schedule: Elements of the Quality System shall be reviewed on a regularly scheduled basis. These elements include the following main sections: equipment, test method, and documentation.
Process Control:
Prior to performing the audit, a plan should be prepared containing the following information: scope of the audit, auditor's name, date of the audit, and audit checklist. This plan is communicated to each manufacturer to be audited in advance of the auditor arriving at their facility. A written set of questions shall be developed for each audit prior to beginning. This Audit Checklist shall be communicated to the manufacturer before the auditor arrives. At the conclusion of each audit, the auditing entity shall publish a written report. The audit report shall highlight any non-conformances. Major non-conformances may result in non-certification or probation until effective written corrective action is submitted to the auditing entity for review.

Minor non-conformances are not cause for non-certification or probation. Written corrective action will be submitted to the auditing entity for review. Manufacturer Management shall respond to the auditing entity in writing indicating how discrepancies noted during the audit were corrected. These responses will be maintained in the customer's confidential file and used during subsequent audits. Corrective action is further explained in Example 7.

The following items are considered to be official audit records and shall be maintained by the auditing entity and the Manufacturer Management for a minimum of five years: audit report, corrective action response to non-conformances, and completed assessment checklist and assessor's working papers.

Example 7

Corrective Action System

This Example presents a standard method for responding to non-conformances from the auditing entity, certification audit non-conformances, and abnormal results for auditing entity Reference Lens.
Procedure:
Any non-conformance issued requires documented corrective action using an appropriate form. Failure to respond to non-conformances can result in disciplinary action being taken against the certified manufacturer including probation of the manufacturer from the FDA Compliance Program, suspension of certification and ultimately revocation of certification. In the analysis of a non-conformance, the root cause shall be determined (where appropriate) before corrective action is taken. Non-conformances should be evaluated to determine their impact on the FDA Compliance Program. Corrective action should be implemented based on the degree of impact of the non-conformance. Corrective Action Requests (CARs) will be issued to the individual identified as the contact person for the manufacturer. The corrective action taken shall be sufficient to adequately address the non-conformance. The root cause and corrective actions are documented on the CAR form and must be returned to the auditing entity within thirty days. The auditing entity will review the root cause identification and corrective action listed. If the review determines the root cause and corrective action listed are appropriate for the non-conformance, the CAR will be filed in the customer's FDA file. The response must include documented evidence that the corrective action stated is occurring. The customer will be advised on the status of the CAR. If the review determines the root cause and corrective action listed are not appropriate for the non-conformance or that the documented evidence accompanying the corrective action is not sufficient, the customer will be advised and re-evaluation of the root cause and/or corrective action will be required by the customer. Review will continue until the response is determined to be appropriate.

On the next scheduled audit of the program, the assessor will review the CAR and conduct an on-site assessment of the effectiveness of the corrective action. The on-site assessor will close the CAR if the corrective action is determined to be effective. The manufacturer may request an extension to the thirty-day time to return the CAR. The request must include the reason(s) for the extension and the proposed date the CAR will be returned. The auditing entity will evaluate the request and if approved notify the customer. If the request is not approved or requires modification the auditing entity will notify the customer. The auditing entity will document the request and disposition determination in the customer's file.

The manufacturer may challenge the non-conformance and resulting CAR. This challenge must contain information relating to why the manufacturer believes the non-conformance and CAR to be unwarranted. The auditing entity will evaluate the challenge and if it is justified, the CAR will be recalled. If the evaluation determines that a CAR is appropriate, the auditing entity will notify the manufacturer. The auditing entity will document the challenge and disposition determination in the customer's file.

Example 8

Data Records and Retention

This Example defines the records that must be maintained in order to meet record retention requirements associated with the impact resistance test program.
Procedure:
Data Records shall be filled out at the time the work is done. The manufacturer must maintain the following records: how lenses were rendered impact resistant, when the lenses were tested for impact resistance, how the lenses were tested for impact resistance, who tested the lenses for impact resistance, the audits conducted on the manufacturer's system of impact testing, calibration records, maintenance records, copies of invoice(s), shipping document(s), and records of sale or distribution of all impact resistance prescription eyeglasses and sunglasses. All records must be maintained for at least three years.

Example 9

Process Control

This Example identifies methods for the manufacturer to implement and document process control to meet the requirements for the auditing entity's Compliance Program.
Procedure:
Process control consists of four elements under the program. They are: preventive maintenance of surfacing equipment, backside coating equipment, and edging machines; process control monitors showing the spindle speed, targets and tolerances of the coating units (this normally includes speeds for wash, coat and spin off); documentation showing that regular change out of the UV cure bulb is occurring at the intervals recommended by the manufacturer; a documented system indicating what to do when things are not operating properly for generator failures, cylinder machine failures, cleaning line failures, coating unit failures, and edging machine failures. Each of these elements is addressed in the following sections. Preventive maintenance is regularly scheduled maintenance of equipment. It is not unscheduled maintenance that is a result of equipment failure. Spindle speeds on the coating units should be monitored and recorded on a regular basis. The interval of the monitoring is a decision that is left to manufacturer management. Typically monitoring is on a daily basis in single shift operations, and by shift in multi-shift operations.

For manufacturers using a UV cure process, changing the UV bulb at regular intervals (recommended by the manufacturer of the system) is required. If no recommendation is available from the manufacturer, bulbs are typically changed at one thousand hours of use. A documented system indicating what to do when things are not operating properly is required. This can be as simple as a written policy statement saying to contact your supervisor (or maintenance) when a machine has problems. It can be as complex as a series of documents that identify troubleshooting techniques and repair instructions. The complexity of this program is left to the discretion of manufacturer management and should be based on resources available. However, the policy must be in writing and signed and dated by the responsible authority.

Example 10

Variable Height Impact Test (i.e., "Up-Down" Method)

This procedure provides a guideline to perform impact resistance tests on ophthalmic lenses, using the variable height method.
Material and Equipment:
One 5/8-inch steel ball weighing not less than 16 grams, variable height impacting worksheet, magnetic release variable height impacting machine, digital center thickness gauge with two (2) decimal place resolution using a millimeter scale, and test lenses. 55 or 12 lenses must be supplied (depending on which test is selected). The recommended lens configuration for normal testing is −2.00D sphere power, at a consistent center thickness edged to 54 mm, S-10 shape with a V-safety bevel. For FDA Testing the lens must be finished to the reference lens configuration.
Procedure:
Condition lenses. Assign a number to each lens (1 through 12, 1 through 55, etc.) by marking them on the edge of the convex side. Measure and record the center thickness of each lens. Fill in an appropriate form (e.g., Variable Height Impacting Worksheet) as completely as possible at the beginning of the test with: Test date, manufacturer, trade name, material, base, power, coating types, and name of technician performing the test. For groups where historical data is available (i.e. FDA Compliance Program) this data should be used to determine the starting height and interval. If no data is available, proceed as follows. Select the last lens for use in determining the impact test starting height. Note: these results are not to be used in impact analysis. Visually center the edged test lens over the lens support base convex side up. Impact the lens at 100 inches. If a fracture does not occur, double the height and impact the same lens. If a fracture does occur, halve the height and impact a lens. Repeat the doubling or halving until a reasonable estimate of the start height is made. For lenses that do not break at 200" (the maximum height of the variable impact tester), switch testing to the pneumatic impact tester. See Example 11 below for test procedure.

Once the starting height has been determined, impact the remaining lenses using the "up and down" method as follows. Note all lenses will be impacted only once. Visually center the edged test lens over the lens support base—convex side up. Since the starting point has already been established, bring the ball up to that height, and drop the ball to impact the lens by hitting the De-Mag button. If the lens fractures, decrease (or drop) the height on the next lens by 5 inches for 55 piece groups, 10 inches for 12 piece groups or by the interval determined using historical data if it is available. If the lens does not fracture, increase the drop height on the next lens by 5 inches for 55 piece groups, 10 inches for 12 piece groups or by the interval determined using historical data if it is available. Repeat this "up and down method" until all lenses have been impacted. Note: Fractures should be recorded with an "X" on the impacting worksheet, non-fractures should be recorded with an "O". The height at which the ball was dropped must also be recorded.

Input all lenses including lenses used to establish starting impact height into the CIS. Any lenses not included in the impact analysis should have a comment entered explaining why they are not included.
Assessment:

Data input into the auditing entity's Information System (e.g., database) calculates an average fracture height and percent of lenses fractured. For groups tested under the FDA Compliance Program described herein, a statistical analysis is run using regression statistics to determine the median fracture height (50th percentile) and the lower confidence level (at a 99% confidence interval) for the 6.5 percentile fracture point.

Example 11

Variable Height Pneumatic Impacting

This procedure provides a guideline to perform impact resistance tests on ophthalmic lenses, using the pneumatic impact variable height method.
Materials and Equipment:

One ⅝-inch steel ball weighing not less than 16 grams, Pneumatic Assist Unit, Impacting Worksheet or other suitable form, Digital center thickness gauge with two (2) decimal place resolutions using a millimeter scale, and test lenses. 55 or 12 lenses are supplied (depending on which test is selected). The recommended lens configuration for normal testing is −2.00D sphere power, at a consistent center thickness edged to 54 mm, S-10 shape with a V-Safety bevel or as requested by the customer. For FDA Testing the lens is finished to the reference lens configuration.
Procedure:

Condition Lenses. Assign a number to each lens (1 through 12, 1 through 55, etc.) by marking them on the edge of the convex side of the lens. Measure and record the center thickness of each lens. Fill in an appropriate form (e.g., Air Assist Impacting Worksheet) as completely as possible at the beginning of the test with: Test Date, Manufacturer, Trade Name, Material, Base, Power, Coating type, and Name of Technician performing the test. Turn on the digital pressure gage on the tester prior to starting up the compressor. This insures there is no residual; pressure in the line that could skew the reading on the digital pressure gage. If it is necessary to check the "zero" on the digital pressure gage after the line is pressurized, close the regulator valve to insure minimal air flow, remove the gage and zero it as needed. Prior to impacting any lenses in the test group the impact tester is qualified. Insert a dummy lens (polycarbonate if available) into the impact tester. Adjust the pressure gage to the PSI noted on the test sheet as the starting pressure. If no starting pressure is given, proceed with Data Reporting as described below prior to completing this section. Fire the ball and note the reading in the digital indicator (FPS). Compare the FPS displayed to the data sheet provided for normal FPS values. If the FPS value displayed is outside the control limits for the PSI setting used contact the quality manager.

Repeat the steps above for setting one increment above and one increment below the starting PSI. For groups where historical data is available (i.e. FDA Compliance Program) this data is used to determine the starting height and interval. If no data is available, proceed as follows. Select the last lens for use in determining the impact test starting height. Note: these results are not to be used in impact analysis. Visually center the edged test lens over the lens support base convex side up. Record the pressure setting for the lens on the impacting worksheet in the PSI column. Impact the lens at 20 PSI. If a fracture does not occur, double the PSI and impact the same lens. If a fracture does occur, halve the PSI and impact a lens. Repeat the doubling or halving until a reasonable estimate of the starting PSI is made. The maximum pressure to be used is 60 PSI. Note: If no fracture occurs at 60 PSI, begin impacting lenses at 60 PSI. If no fractures are noted, impact all lenses at 60 PSI. If a fracture is noted at 60 PSI, contact the appropriate personnel at the manufacturer (e.g., manager) for instructions on how to proceed.

Once the starting pressure is determined, impact the remaining lenses using the "up and down" method as follows. Note: All lenses are impacted only once. Visually center the edged test lens over the lens support base, convex side up. Insert the ball into the guide tube. Check the release air pressure and make final adjustments, if required. Record the pressure setting for that lens (e.g., on the Impacting Worksheet, in the PSI column). Close the doors. Press the firing button. Compare the FPS displayed to the data sheet provided for normal FPS values. If the FPS value displayed is an outlier (outside the control limits for the PSI setting used) record the calculated FPS value from the normal FPS data sheet. Otherwise, record the value displayed on the FPS display. Record the mode (e.g., on the impacting worksheet in the X/O column) where X=break and O=no break. If the test lens broke, decrease the air pressure by 1 PSI (for 55 piece groups, 2 PSI for 12 piece groups, or by the interval determined using historical data if it's available) for the next lens. If the test lens did not break, increase the air pressure by 1 PSI (for 55 piece groups, 2 PSI for 12 piece groups, or by the interval determined using historical data if it's available) for the next lens. Repeat this "up and down" method until all lenses are impacted. With each lens impacted, note on the worksheet the PSI, an X for break and O for no break, and the FPS. Note: any increase or decrease in release air pressure should be maintained in fixed steps through out the test.
Data Reporting:

Input all lenses including lenses used to establish starting impact height into the CIS. Any lenses not included in the impact analysis have a comment entered explaining why they are not included. CIS calculates height from the FPS values.
Assessment:

Data input into the auditing entity's Information System (e.g., database) calculates an average fracture height and percent of lenses fractured. For groups tested under the FDA Compliance Program described herein, a statistical analysis is run using regression statistics to determine the median fracture height (50th percentile) and the lower confidence level (at a 99% confidence interval) for the 6.5 percentile fracture point.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for ensuring that plastic ophthalmic lenses produced by a lens manufacturer are compliant with lens impact resistance regulations, the method comprising the steps of:
   (a) the lens manufacturer providing an auditing entity with information about the type of lenses it manufactures and whether the lenses have been treated with a coating selected from the group consisting of a hard coating and an anti-reflective coating;
(b) the auditing entity using the information about the type of lenses and whether the lenses have been treated with a coating to determine the lens manufacturer's weakest lens configuration;
(c) the lens manufacturer providing the auditing entity with a plurality of reference lenses having the weakest lens configuration;
(d) the auditing entity testing the plurality of reference lenses by impact resistance testing;
(e) the auditing entity providing the lens manufacturer with a plurality of formal operating procedure guidelines governing process control in a process of manufacturing and testing of the lenses;
(f) the auditing entity conducting an initial on-site audit of the lens manufacturer to determine whether the lens manufacturer has implemented the formal operating procedure guidelines;
(g) the auditing entity conducting periodic follow-up on-site audits of the lens manufacturer to determine whether the lens manufacturer has continued to implement the formal operating procedure guidelines; and
(h) the lens manufacturer subjecting a sample set of lenses from a batch of lenses having the weakest lens configuration to an impact resistance test on a daily basis, wherein the sample set comprises lenses having cosmetic defects.

2. The method of claim 1, wherein the number of lenses in the sample set is less than 5.3% of the number of lenses in the batch and the batch of lenses is deemed to be impact resistant if the number of lenses in the sample set that fail the impact resistance test is zero if the batch contains less than 3201 lenses, and no more than one if the batch contains 3201 or more lenses.

3. The method of claim 1, wherein when the number of lenses contained in the batch is in the range of 151 to 280, the size of the sample set is in the range of 6 to 9 lenses.

4. The method of claim 3, wherein the size of the sample set is 8 lenses.

5. The method of claim 1, wherein when the number of lenses contained in the batch is in the range of 281 to 500, the size of the sample set is in the range of 9 to 11 lenses.

6. The method of claim 5, wherein the size of the sample set is 10 lenses.

7. The method of claim 1, wherein when the number of lenses contained in the batch is in the range of 501 to 1200, the size of the sample set is in the range of 11 to 14 lenses.

8. The method of claim 7, wherein the size of the sample set is 12 lenses.

9. The method of claim 1, wherein when the number of lenses contained in the batch is in the range of 1201 to 3200, the size of the sample set is in the range of 14 to 26 lenses.

10. The method of claim 9, wherein the size of the sample set is 15 lenses.

11. The method of claim 1, wherein when the number of lenses contained in the batch is in the range of 3201 to 1 million, the size of the sample set is in the range of 26 to 30 lenses.

12. The method of claim 11, wherein the size of the sample set is 28 lenses.

13. The method of claim 1, wherein the batch has an AQL in the range of 0.5% to 1.5%.

14. The method of claim 13, wherein when the number of lenses contained in the batch is in the range of 151 to 280, the batch has an AQL of 0.6%.

15. The method of claim 13, wherein when the number of lenses contained in the batch is in the range of 281 to 500, the batch has an AQL of 0.6%.

16. The method of claim 13, wherein when the number of lenses contained in the batch is in the range of 501 to 1200, the batch has an AQL of 0.4%.

17. The method of claim 13, wherein when the number of lenses contained in the batch is in the range of 1201 to 3200, the batch has an AQL of 0.3%.

18. The method of claim 13, wherein when the number of lenses contained in the batch is in the range of 3201 to 1 million, the batch has an AQL of 1.3%.

* * * * *